United States Patent [19]

Kreh et al.

[11] Patent Number: 5,043,099

[45] Date of Patent: Aug. 27, 1991

[54] MONO- AND DI-SUBSTITUTED (DIPHOSPHONOALKYLAMINO METHYL)-4-HYDROXYBENZENESULFONIC ACID

[76] Inventors: Robert P. Kreh, 8008 Cipher Row, Jessup, Md. 20794; Charles G. Carter, 9524 Bruce Dr., Silver Spring, Md. 20901

[21] Appl. No.: 554,041

[22] Filed: Jul. 13, 1990

[51] Int. Cl.$^5$ .............................................. C23F 11/10
[52] U.S. Cl. ................................. 252/389.22; 562/13; 252/389.62
[58] Field of Search ...................... 562/13; 252/389.22, 252/389.62

[56] References Cited

U.S. PATENT DOCUMENTS

| | | | |
|---|---|---|---|
| 2,673,213 | 3/1954 | Berworth | 562/14 |
| 3,398,198 | 8/1968 | Kersnar | 564/477 |
| 4,085,134 | 4/1978 | Redmore et al. | 562/14 |
| 4,229,294 | 9/1980 | Redmore et al. | 204/255 |
| 4,312,736 | 1/1982 | Menth et al. | 562/14 |
| 4,608,368 | 8/1986 | Blum et al. | 562/13 |

FOREIGN PATENT DOCUMENTS

| | | |
|---|---|---|
| 2048913 | 4/1972 | Fed. Rep. of Germany . |
| 2625767 | 12/1977 | Fed. Rep. of Germany . |
| 48912 | 12/1989 | U.S.S.R. . |

OTHER PUBLICATIONS

Helv. Chim. Acta 35 1785 (1952).

*Primary Examiner*—Deborah L. Kyle
*Assistant Examiner*—Valerie Fee
*Attorney, Agent, or Firm*—Howard J. Troffkin

[57] ABSTRACT

New polyamino-polyphosphonic-hydroxybenzenesulfonic acid compounds as the free acid or their alkali or alkaline earth metal salt. Specifically, the compounds are the mono- and di-(1,1-diphosphono-1-alkylaminomethyl)-4-hydroxybenzenesulfonic acid. These compounds are useful as corrosion inhibiting agents for metal/water applications.

10 Claims, No Drawings

MONO- AND DI-SUBSTITUTED (DIPHOSPHONOALKYLAMINO METHYL)-4-HYDROXYBENZENESULFONIC ACID

BACKGROUND OF THE INVENTION

The present invention is directed to certain new polyamino-polyphosphono hydroxybenzenesulfonic acid compounds and to aqueous compositions containing said compounds. Specifically, the novel compounds of the present invention are 3,5-bis(1,1-diphosphonoalkylaminomethyl)-4-hydroxybenzenesulfonic acid and 3-(1,1-diphosphonoalkylaminomethyl)-4-hydroxybenzenesulfonic acid.

The subject compounds either singly or in combination, can be incorporated into aqueous solutions (normally as a metal salt) and utilized as a metal chelant to prevent scale and corrosion formation in aqueous systems.

Various organic acid compounds have been synthesized to provide a material useful as a scale and corrosion inhibiting agent. These agents contain various organic groups in certain stereoconfiguration to provide the ability to act as a chelant for metal ions.

Amino acids are well known to provide chelant properties. For example, U.S. Pat. No. 2,673,213 teaches that polyamino acids of carboxylic, phosphonic or sulfuric acids are capable of reacting with relevant metal ions to form the chelant. DE 20 48 9 13 and 26 25 767 teach that 1-amino-1,1-diphosphonic acid are capable of complexing with metal ions and that they can be formed by reacting an organic nitrile with phosphorous acid in the presence of HX or at elevated temperatures in the absence of HX.

The desire to incorporate hydroxyalkyl functional groups into phosphonic acid metal chelating compounds is described in U.S. Pat. No. 3,398,198. This reference suggests that hydroxyalkyl groups can be substituted for a hydrogen of an amine by reaction with an alkylene oxide (e.g. propylene oxide).

Various amino-phosphonic-sulfonic acids are taught in U.S. Pat. Nos. 4,085,134; 4,312,736; and 4,229,294. These patents are directed to compounds having the general formula:

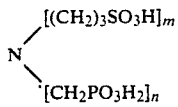

where N is an amine group and n and m are each at least 1 which are formed by reacting an amine with phosphorous acid in the presence of a strong mineral acid.

In *Helv. Chim. Acta*, 35 1785 (1952) various phenolic compounds were synthesized to study their complexing capabilities. Included were amino-carboxylic-hydroxybenzenesulfonic acid compounds by the reaction of phenolsulfonic acid, formaldehyde and iminodiacetic acid. Iminodiacetic acid, being a relatively unhindered secondary amino compound, readily gave a clean reaction (due to the single deprotonation at the amine and the amine group being connected the each carboxylic acid via a secondary carbon atoms).

The general trend in all of the above described efforts has been to form compounds having a multiplicity of functional groups in a configuration which enables them to be capable of chelating with metal ions. Thus, compounds with multiple functional groups exhibits enhanced ability of scale and corrosion control because they have greater complexing ability and/or solubility in aqueous solutions.

It is highly desired to have phosphonic acid compounds which are highly substituted and further contain other groups, including amino and hydroxy, in close proximity within the compounds structure. This combination provides a compound having good metal complexing capabilities.

SUMMARY OF THE INVENTION

The present invention is directed to certain novel compounds which are the aminophosphonic acid derivatives of phenolsulfonic acids:-3,5-bis(1,1-diphosphonoalkylaminomethyl)-4-hydroxybenzenesulfonic acid and 3-(1,1-diphosphonoalkylaminomethyl)-4-hydroxybenzenesulfonic acid, and to compositions comprising one or more of said acids.

DETAILED DESCRIPTION OF THE INVENTION

The present invention is directed to certain novel compounds and to compositions formed therefrom. Specifically, the compounds are 3,5-bis(1,1-diphosphonoalkylaminomethyl)-4-hydroxybenzenesulfonic acid having the formula:

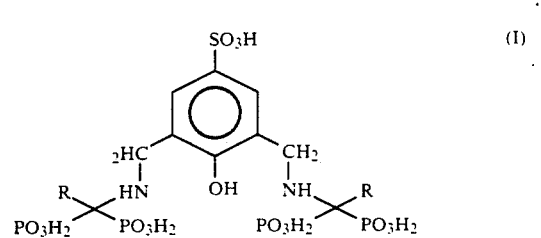

and 3-(1,1-diphosphonoalkylaminomethyl)-4-hydroxybenzenesulfonic acid having the formula:

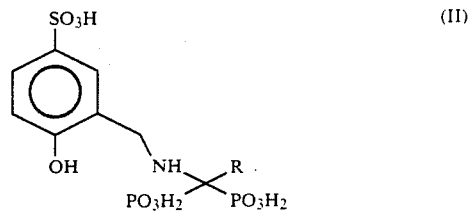

in which R represents hydrogen or a methyl or ethyl group and their alkali and alkaline earth metal salts. The most desired compounds are those in which each R is a methyl group.

The subject compounds have been formed by reacting a 1,1-diphosphono-alkylamine (alkyl is methyl, 1-ethyl or 1-propyl) formaldehyde and 4-phenolsulfonic acid (herein after "aromatic compound") in the manner described herein below in detail. The compounds described above in which R is methyl are formed from 1,1-diphosphonoethylamine.

The reactants are each available compounds which can be obtained from commercial sources. Further, the reactant, 1,1-diphosphono-alkylamine (hereinafter "amine compound") can be formed (when R is alkyl) by the reaction of phosphorous acid with the appropriate nitrile (acetonitrile or propionitrile) in the manner described in U.S. Pat. No. 4,239,695. The amine compound reactant (when R is hydrogen), 1-aminoalkylidene 1,1-diphosphonic acid can be formed by the reaction of $HCONH_2$ with $PCl_3$ and $H_3PO_3$ in the manner described in Z. Anorg Allg. Chem. 1972, 389(2), 119-128.

The formaldehyde reactant can be supplied by any of its known forms as, for example, paraformaldehyde or aqueous formaldehyde solution. The latter is preferred because of ease of handling.

The reactants are contacted together in an inert mutual solvent, such as water, alcohol (preferably a $C_1$-$C_3$ alcohol), dimethylformamide, dimethylsulfoxide or other polar solvent. The preferred solvent is water.

The synthesis is carried out by introducing the above-stated reactants into the inert solvent and adding a small amount of a base, such as an alkali or alkaline earth metal hydroxide, oxide, carbonate or the like. The preferred base are hydroxide of alkali metals, most preferably potassium hydroxide.

The reaction solution should be maintained at a basic pH, preferably at least 7.5 and most preferably from about 7.5 to 9. The reaction solution should be maintained at an elevated temperature of from about 40° to 100° C. Although lower temperatures may be used, the desired product is achieved only after an extended period of time. High temperatures should be avoided as such condition causes lowering of yield of desired product due to the products degradation or polymerization. The reaction will provide the optimum yield of material in a time which is inversely proportioned to the reaction temperature utilized. The reaction time is normally between 2 to 72 hours. For example, a reaction carried out at 40° C. will take about 72 hours; when run at 65° C. it will take about 16 hours; and when run at 100° C., it will take 2 to 5 hours.

The molar ratio of reactants will control the product that is formed. To form compound I, the reactants should be in molar amounts such that for each mole of aromatic reactant used, one uses at least 2 moles of formaldehyde (preferably from 2.1 to 3 moles and most preferably about 2.4 to 2.6 moles) and at least about 2 moles of the amine reactant (preferably from 2.1 to 2.5 moles and most preferably about 2.1 to 2.3 moles). The product (I) is normally produced in very high yields, with yields of greater than 90 percent (based on the aromatic reactant) being attainable. The resultant liquid containing product (I) can be directly used as a corrosion control composition. The reaction liquid, being a polar solvent is miscible with aqueous mediums requiring treatment. Alternately, product (I) can be separated from the liquid by conventional methods, such as precipitation into a non-solvent or formation of a metal salt which is insoluble in the reaction liquid.

Compound II is formed when the ratio of reactants are adjusted to limit the amount of formaldehyde and amine reactants used in relation to the aromatic reactant. For each mole of aromatic reactant, the reaction should utilize about 1 to 1.5 moles of each of the other two reactants, preferably from about 1.05 to 1.3 moles. The amount of amine may be further limited to from 1 to about 1.2 moles to achieve high yields of the monosubstituted compound (II). Compound II is the precursor to compound I and the greater the amount of amine present the lower the yield of compound (II) with comparatively greater amounts of compound (I) produced. Compound (I) and (II) both have a high degree of chelating ability and, therefore, the liquid reaction product solution can be directly used as a chelating composition for corrosion inhibiting properties and the like.

The following examples are given for illustrative purposes only and are not meant to be a limitation on the invention, as defined by the claims appended hereto. All parts and percentages are by weight unless otherwise indicated.

EXAMPLE I

Synthesis of 3,5-bis(1,1 diphophonoethyl-aminomethyl)-4-hydroxybenzenesulfonic acid.

8 parts of 4-hydroxybenzenesulfonic acid (as its sodium salt dihydrate), 16 parts of 1,1 diphosphonoethylamine and 7 parts of aqueous formaldehyde (37% sol.)-were introduced into 50 parts of water. The pH of the solution was adjusted to 7.5 with approximately 25 parts of aqueous KOH (45% sol.). The solution was heated and maintained to 40° C. while stirring for 5 days.

A sample of the resultant solution was evaporated under vacuum to remove the water solvent. The solid was taken up in $D_2O$ and analyzed using proton magnetic resonance. The product's spectrum at a pH of 7.5 was characterized by a singlet at 7.65 ppm (parts per million) and at 4.56 ppm and a triplet at 1.72 ppm. The reference $H_2O$ peak was at 4.84 ppm. The spectrum indicated a yield of 95% for the desired product.

EXAMPLE II

Synthesis of 3-(1,1-diphophonoethyl-aminomethyl)-4-hydroxybenzenesulfonic acid.

16 parts of 4-hydroxybenzenesulfonic acid (as the sodium salt dihydrate), 16 parts of 1,1 diphosphonoethylamine, and 7 parts of aqueous formaldehyde (37%) were introduced into 100 parts of water. The pH was adjusted to 9.5 with approximately 41 parts aqueous KOH solution (45%). The resultant solution was heated reacted and analyzed as described in Example I above. The proton magnetic resonance spectrum at a pH of 9.5 was characterized by multiplets of 7.66, 7.58 and 6.70 ppm; a singlet at 4.43 ppm and a triplet at 1.70 ppm. The $H_2O$ reference peak was at 4.83 ppm.

We claim:

1. A compound corresponding to the formula:

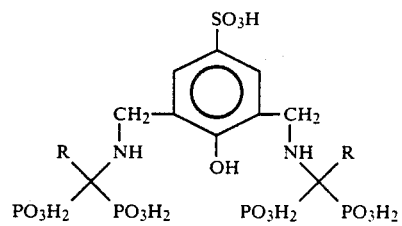

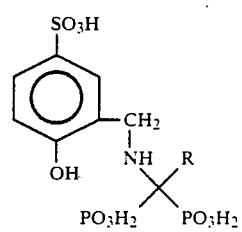

wherein each R represents hydrogen, methyl or ethyl; or an alkali or alkaline earth metal salt thereof.

2. The compound of claim 1 wherein each R represents methyl.

3. The compound of claim 2 wherein said compound is 3,5-bis(1,1-diphosphonoethylaminomethyl)-4-hydroxybenzene sulfonic acid or its alkali or alkaline earth metal salts.

4. The compound of claim 2 wherein said compound is 3-(1,1-diphosphonoethylaminomethyl)-4-hydroxybenzenesulfonic acid or its alkali or alkaline earth metal salts.

5. The compound of claim 3 capable of exhibiting a proton magnetic resonance spectrum at a pH of 7.5 having the following absorption peaks: singlet at 7.65 ppm and at 4.56 ppm and a triplet at 1.72 ppm with a $H_2O$ reference peak at 4.84 ppm.

6. The compound of claim 4 capable of exhibiting a magnetic resonance spectrum at a pH of 9.5 having the following absorption peaks: multiplets at 7.66, 7.58 and 6.70 ppm; singlet at 4.43 ppm; and triplet at 1.70 ppm, with reference $H_2O$ peak at 4.83 ppm.

7. A composition comprising an inert polar solvent containing at least one compound of claim 1 or 2.

8. The composition of claim 7 wherein the inert solvent is water.

9. The composition of claim 7 wherein the solvent contains a mixture of compound I and II.

10. A composition comprising an inert polar solvent containing the compound of claim 3, 4, 5, or 6.

* * * * *